United States Patent
Freeman et al.

(10) Patent No.: US 10,993,664 B2
(45) Date of Patent: *May 4, 2021

(54) DELIVERY OF ELECTRODE GEL USING CPR PUCK

(71) Applicant: ZOLL Medical Corporation, Chelmsford, MA (US)

(72) Inventors: Gary A. Freeman, Waltham, MA (US); Ulrich Herken, Medford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 239 days.

This patent is subject to a terminal disclaimer.

(21) Appl. No.: 16/005,173

(22) Filed: Jun. 11, 2018

(65) Prior Publication Data

US 2018/0289327 A1 Oct. 11, 2018

Related U.S. Application Data

(63) Continuation of application No. 14/167,343, filed on Jan. 29, 2014, now Pat. No. 9,999,393.

(Continued)

(51) Int. Cl.
*A61B 5/00* (2006.01)
*A61B 5/0408* (2006.01)
(Continued)

(52) U.S. Cl.
CPC .......... *A61B 5/6839* (2013.01); *A61B 5/0452* (2013.01); *A61B 5/04085* (2013.01);
(Continued)

(58) Field of Classification Search
CPC .... A61N 1/3968; A61N 1/046; A61N 1/0492; A61N 1/0496; A61B 5/04085;
(Continued)

(56) References Cited

U.S. PATENT DOCUMENTS

| 4,094,310 A | 6/1978 | McEachern et al. |
| 4,632,122 A | 12/1986 | Johansson et al. |

(Continued)

FOREIGN PATENT DOCUMENTS

| EP | 00339471 A2 | 11/1989 |
| EP | 0295497 B1 | 9/1993 |

(Continued)

OTHER PUBLICATIONS

American Journal of Respiratory and Critical Care Medicine, vol. 166, pp. 111-117 (2002). American Thoracic Society ATS Statement: Guidelines for the Six-Minute Walk Test, available at http://ajrccm.atsjournals.org/cgi/content/full/166/1/111.

(Continued)

*Primary Examiner* — Jennifer Pitrak McDonald
*Assistant Examiner* — Pamela M. Bays
(74) *Attorney, Agent, or Firm* — The Webb Law Firm (57) ABSTRACT

An electrode assembly includes a first surface to be placed adjacent a person's skin and a second surface including a plurality of reservoirs of conductive gel. The plurality of reservoirs of conductive gel are disposed on sections of the electrode assembly that are at least partially physically separated and may move at least partially independently of one another to conform to contours of a body of a patient. The electrode assembly is configured to dispense an amount of the electrically conductive gel onto the first surface in response to an activation signal and to provide for a defibrillating shock to be applied to the patient through the amount of the electrically conductive gel.

32 Claims, 11 Drawing Sheets

Related U.S. Application Data (60) Provisional application No. 61/758,063, filed on Jan. 29, 2013.

(51) Int. Cl.
*A61B 5/0452* (2006.01)
*A61N 1/04* (2006.01)
*A61M 16/00* (2006.01)
*A61H 31/00* (2006.01)
*A61N 1/39* (2006.01)

(52) U.S. Cl.
CPC ........ *A61B 5/04087* (2013.01); *A61B 5/6833* (2013.01); *A61N 1/046* (2013.01); *A61N 1/0492* (2013.01); *A61N 1/3968* (2013.01); *A61H 2031/002* (2013.01); *A61M 16/0048* (2013.01); *A61N 1/0496* (2013.01)

(58) Field of Classification Search
CPC . A61B 5/04087; A61B 5/0452; A61B 5/6833; A61B 5/6839; A61H 2031/002; A61M 16/0048
See application file for complete search history.

(56) References Cited

U.S. PATENT DOCUMENTS

| | | |
|---|---|---|
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,305,746 A * | 4/1994 | Fendrock ............ A61B 5/0408 600/391 |
| 5,348,008 A | 9/1994 | Bomn et al. |
| 5,365,932 A | 11/1994 | Greenhut |
| 5,472,453 A | 12/1995 | Alt |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,065,154 A | 5/2000 | Hulings et al. |
| 6,097,982 A | 8/2000 | Glegyak et al. |
| 6,097,987 A | 8/2000 | Milani |
| 6,125,521 A | 10/2000 | Marro et al. |
| 6,128,521 A | 10/2000 | Marro et al. |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,523,303 B2 | 2/2003 | Weder et al. |
| 6,526,303 B1 * | 2/2003 | Scampini ............ A61N 1/046 600/386 |
| 6,681,003 B2 | 1/2004 | Linder et al. |
| 6,690,969 B2 | 2/2004 | Bystrom et al. |
| 6,692,490 B1 * | 2/2004 | Edwards ............ A61B 18/1477 606/41 |
| 6,804,554 B2 | 10/2004 | Ujheli et al. |
| 6,827,695 B2 | 12/2004 | Palazzolo et al. |
| 6,908,437 B2 | 6/2005 | Bardy |
| 6,990,373 B2 | 1/2006 | Jayne et al. |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,488,293 B2 | 2/2009 | Marcovecchio et al. |
| 7,831,303 B2 | 11/2010 | Rueter et al. |
| 7,974,689 B2 | 7/2011 | Volpe et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 2002/0072787 A1 * | 6/2002 | Partridge ............ A61N 1/057 607/122 |
| 2003/0004547 A1 | 1/2003 | Owen et al. |
| 2003/0055477 A1 | 3/2003 | Dupelle et al. |
| 2003/0095648 A1 | 5/2003 | Kaib et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0162587 A1 * | 8/2004 | Hampton ............ A61N 1/39044 607/5 |
| 2005/0049515 A1 | 3/2005 | Misczynski et al. |
| 2005/0131465 A1 | 6/2005 | Freeman et al. |
| 2005/0222295 A1 | 10/2005 | Siegel |
| 2006/0036292 A1 | 2/2006 | Smith et al. |
| 2006/0085049 A1 | 4/2006 | Cory et al. |
| 2006/0270952 A1 | 11/2006 | Freeman et al. |
| 2007/0118056 A1 | 5/2007 | Wang et al. |
| 2007/0135699 A1 * | 6/2007 | Ward ............ A61B 5/14532 600/373 |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0004686 A1 | 1/2008 | Hunt et al. |
| 2008/0030656 A1 | 2/2008 | Watson et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0249591 A1 | 10/2008 | Gaw et al. |
| 2008/0306560 A1 | 12/2008 | Macho et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicak et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0234716 A1 | 9/2010 | Engel |
| 2010/0241181 A1 | 9/2010 | Savage et al. |
| 2010/0298899 A1 | 11/2010 | Donnelly et al. |
| 2011/0184269 A1 * | 7/2011 | Sauter-Starace ..... A61B 5/0478 600/378 |
| 2011/0288604 A1 * | 11/2011 | Kaib ............ A61N 1/046 607/5 |
| 2011/0288605 A1 | 11/2011 | Kaib et al. |
| 2011/0312644 A1 | 12/2011 | Silverbrook et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |

(56) References Cited

U.S. PATENT DOCUMENTS

2012/0158075 A1    6/2012   Kaib et al.
2013/0267811 A1    10/2013   Pryor et al.

FOREIGN PATENT DOCUMENTS

| EP | 0335356 B1 | 3/1996 |
|----|------------|--------|
| EP | 1455640 B1 | 1/2008 |
| EP | 1720446 B1 | 7/2010 |
| JP | 5115450 A | 5/1993 |
| WO | 200002484 A1 | 1/2000 |
| WO | 2004054686 A1 | 7/2004 |

OTHER PUBLICATIONS

DeBock et al., "Captopril treatment of chronic heart failure in the very old", J. Gerontol. (1994) 49: M148-M152.
O'Keeffe et al., "Reproducability and responsiveness of quality of life assessment and six minute walk test in elderly heart failure patients", Heart (1998) 80: 377-382.

* cited by examiner

DELIVERY OF ELECTRODE GEL USING CPR PUCK

RELATED APPLICATIONS

This application is a continuation of U.S. patent application Ser. No. 14/167,343, entitled "DELIVERY OF ELECTRODE GEL USING CPR PUCK" filed Jan. 29, 2014, now issued as U.S. Pat. No. 9,999,393, which claims priority to U.S. Provisional Application Ser. No. 61/758,063, titled "DELIVERY OF ELECTRODE GEL USING CPR PUCK," filed on Jan. 29, 2013, which are each herein incorporated by reference in their entirety.

BACKGROUND

1. Field of the Invention

The present invention is directed to medical electrodes and electrode systems, and more particularly, to medical electrodes that may be used with a medical device, such as a defibrillator, which may be supplied with a conductive electrode gel prior to administration of an electrical charge to a subject through the medical electrodes.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival.

SUMMARY

In accordance with an aspect of the present invention, there is provided an electrode system. The electrode system comprises a compression device including a first gel reservoir. The first gel reservoir is configured to retain a conductive gel and to release the conductive gel responsive to compression of the compression device. The electrode system further comprises a first therapy pad configured to deliver a defibrillation pulse and a first conduit fluidly connecting the first gel reservoir to the first therapy pad.

In accordance with some embodiments, the system further comprises a second therapy pad.

In accordance with some embodiments, the system further comprises a second conduit fluidly connecting the first gel reservoir to the second therapy pad.

In accordance with some embodiments, the conductive gel is a first conductive gel and the compression device further includes a second gel reservoir in fluid communication with the second therapy pad. The second gel reservoir is configured to retain a second conductive gel and to release the second conductive gel responsive to compression of the compression device.

In accordance with some embodiments, the system further comprises a sensor configured to provide an indication of release of the conductive gel from the first gel reservoir.

In accordance with some embodiments, the sensor comprises a conductivity sensor disposed within the first therapy pad.

In accordance with some embodiments, the sensor comprises a pressure sensor disposed in the compression device.

In accordance with some embodiments, the pressure sensor is disposed within the first gel reservoir.

In accordance with some embodiments, the sensor comprises a valve disposed between the first gel reservoir and the first therapy pad.

In accordance with some embodiments, the sensor comprises a meter configured to measure an impedance between the first therapy pad and the second therapy pad.

In accordance with some embodiments, the first therapy pad includes a backing layer having a front surface configured to adhere to skin of a subject and a rear surface, a plate having a rear surface coupled to the front surface of the backing layer and a front surface that includes a conductive material layer, an electrical lead in electrical contact with the conductive material layer, and an adhesive film border formed on the front surface of the backing layer and defining a conductive gel cavity, the conductive gel cavity surrounded by the adhesive film border on all sides in a plane substantially parallel to the front surface of the backing layer, the conductive gel cavity in fluid communication with the first conduit.

In accordance with some embodiments, the backing layer is substantially impermeable to water and substantially permeable to air.

In accordance with some embodiments, the backing layer comprises expanded polytetrafluoroethylene.

In accordance with some embodiments, the adhesive film border comprises a light curable adhesive.

In accordance with some embodiments, the adhesive film border comprises an ultraviolet light curable adhesive.

In accordance with some embodiments, the system further comprises a source of ultraviolet light coupled to the first therapy pad.

In accordance with some embodiments, the source of ultraviolet light comprises a light emitting diode.

In accordance with some embodiments, the system further comprises a light guide configured and arranged to supply ultraviolet light to substantially all of the adhesive film border.

In accordance with some embodiments, one of the source of ultraviolet light and the light guide is at least partially disposed within the adhesive film border.

In accordance with some embodiments, the adhesive film border comprises epoxy.

In accordance with some embodiments, the first therapy pad includes a plurality of protrusions configured and arranged to facilitate adhesion of the first therapy pad to skin of a subject.

In accordance with some embodiments, the plurality of protrusions comprise barbs configured to penetrate an outer surface of the skin of the subject.

In accordance with some embodiments, the plurality of protrusions are configured to retain the first therapy pad in place on the skin of the subject.

In accordance with some embodiments, the barbs are biodegradeable.

In accordance with some embodiments, the barbs are conductive.

In accordance with some embodiments, the plurality of protrusions comprise carbon nanofibers.

In accordance with some embodiments, the system further comprises a convex applicator for the first therapy pad.

In accordance with another aspect, there is provided a therapy electrode. The therapy electrode comprises a backing including a front surface and a rear surface, an electrolyte reservoir configured to release electrolyte onto the front surface of the backing responsive to application of a compressive force to the therapy electrode, and a plurality of barbs extending from the front surface of the backing and configured to penetrate an outer layer of skin of a subject and retain the therapy electrode in place on the skin of the subject.

In accordance with some embodiments, the barbs are biodegradeable.

In accordance with some embodiments, the barbs are conductive.

In accordance with some embodiments, the barbs comprise carbon nanofibers.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Figure 1:
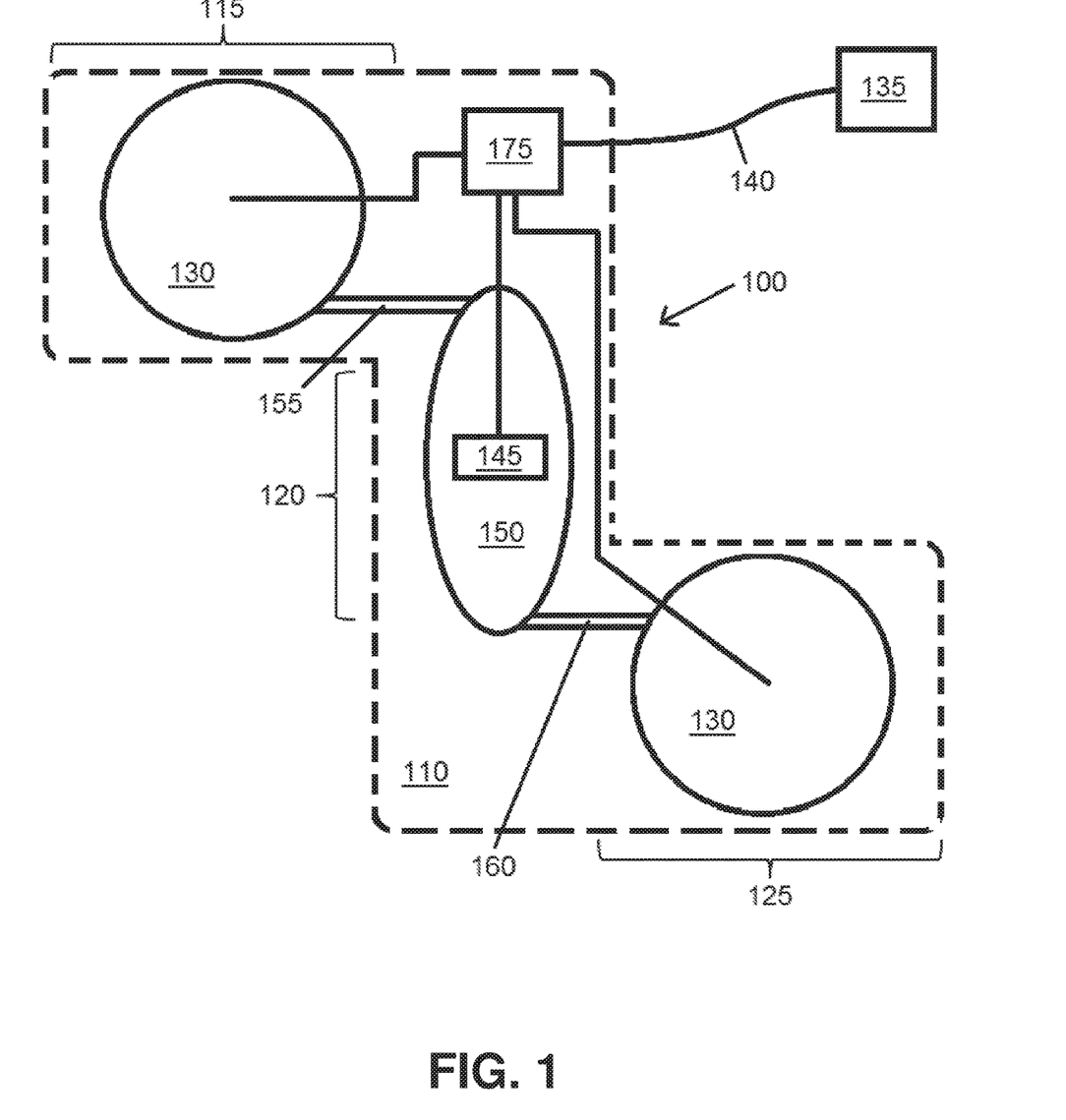
FIG. 1 is a schematic illustration of an electrode system.
Figure 2:
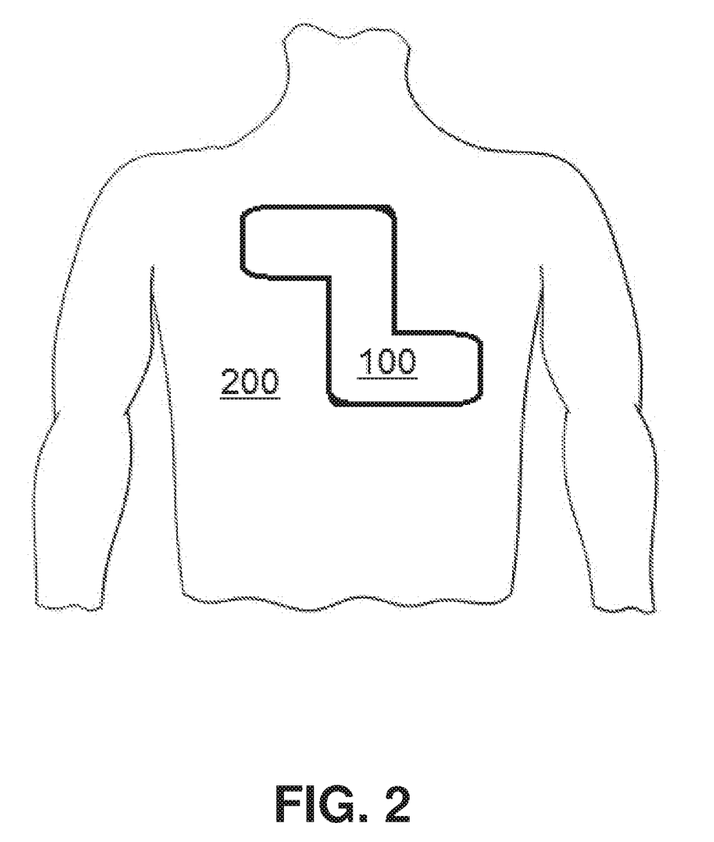
FIG. 2 illustrates the electrode system of FIG. 1 applied to the torso of a subject.

FIG. 1 is a schematic illustration of an electrode system, indicated generally at 100, which may be utilized in, for example, an automated external defibrillator (AED) device, although embodiments of the electrode system may also or alternatively be used with other types of cardiac monitoring and/or treatment devices. Examples of AED devices include Advanced Life Support (ALS) AED devices, such as the E Series, M Series, R Series, or X Series defibrillators, as well as Basic Life Support (BLS) AED devices, such as the AED Pro or AED Plus defibrillator, each available from ZOLL Medical Corporation of Chelmsford, Mass. The electrode system 100 may be placed on or secured to a torso of a subject 200, as illustrated in FIG. 2, to provide treatment, for example, defibrillation.

As shown in FIG. 1, the electrode system 100 includes packaging 110, which is indicated in FIG. 1 in dotted lines so as not to obscure the internal components of the electrode system 100. The packaging 110 includes a substrate upon which other components of the electrode system are mounted. The packaging 110 may be formed of a fabric, for example, cotton, or a plastic material. Embodiments of the present invention are not limited to any particular material of construction of the packaging 110. The packaging 110 defines a first therapy pad 115, a central region including a compression device 120, and a second therapy pad 125.

Each therapy pad 115, 125, includes an electrode 130. The electrodes 130 are electrically coupled to a controller 135 which is in some embodiments located external to the electrode system 100, for example, through an electrical connector 175 and electrical conductor(s) 140. The controller is configured to deliver an electrical charge to the electrodes 130 as needed. The controller 135 may be supplied with power from an external source of power or by a battery, capacitor, battery and capacitor, or other electrical energy storage apparatus electrically coupled to the electrode system 100.

The therapy pads and electrodes are illustrated in FIG. 1 as formed together in one integrated structure, however, in other embodiments, the therapy pads and/or electrodes may be provided in distinct packages on separates substrates. The distinct electrode/therapy pad packages may be coupled together by, for example, conduits for conductive electrode gel and/or electrical cables.

When placed on a subject to be treated by cardio pulmonary resuscitation (CPR), the central region of the packaging of the electrode system 100 provides a location at which a CPR administrator may apply compressions through the electrode system 100 to the chest of the subject. The central region of the packaging may include an accelerometer 145 which may monitor the frequency, depth, and intensity of compressions applied to the subject and supply this information to the controller 135. The controller 135 may provide feedback, for example, through a speaker or display (not shown), to a CPR administrator based on the information supplied by the accelerometer regarding the sufficiency of the chest compressions or the need to increase or decrease the frequency, depth, or intensity of the compressions.

In accordance with one embodiment, the compression device 120 includes a gel reservoir 150. The gel reservoir holds a conductive electrode gel. The conductive electrode gel is retained in the gel reservoir until needed. In some embodiments, responsive to compression of the compression device 120, the gel reservoir releases the conductive electrode gel and supplies the conductive electrode gel to surfaces of the electrodes 130 through conduits 155, 160 in fluid communication between the gel reservoir 150 and the electrodes 130. In some embodiments, the conductive gel is retained within the gel reservoir by membranes at one or both ends of the conduits 155, 160 which are configured to rupture upon the application of sufficient pressure to the compression device. In other embodiments, the conductive gel is retained within the gel reservoir by mechanical valves at one or both ends of the conduits 155, 160 which are configured to open upon the application of sufficient pressure to the compression device. Alternatively, the accelerometer 145 or a pressure sensor in the gel reservoir may supply a signal to the controller 135 responsive to compression of the compression device and the controller may provide a signal to open one or more mechanical valves in fluid communication between the gel reservoir 150 and the electrodes 130. The mechanical valves may be located, for example, at one or both ends of the conduits 155, 160.

Figure 3:
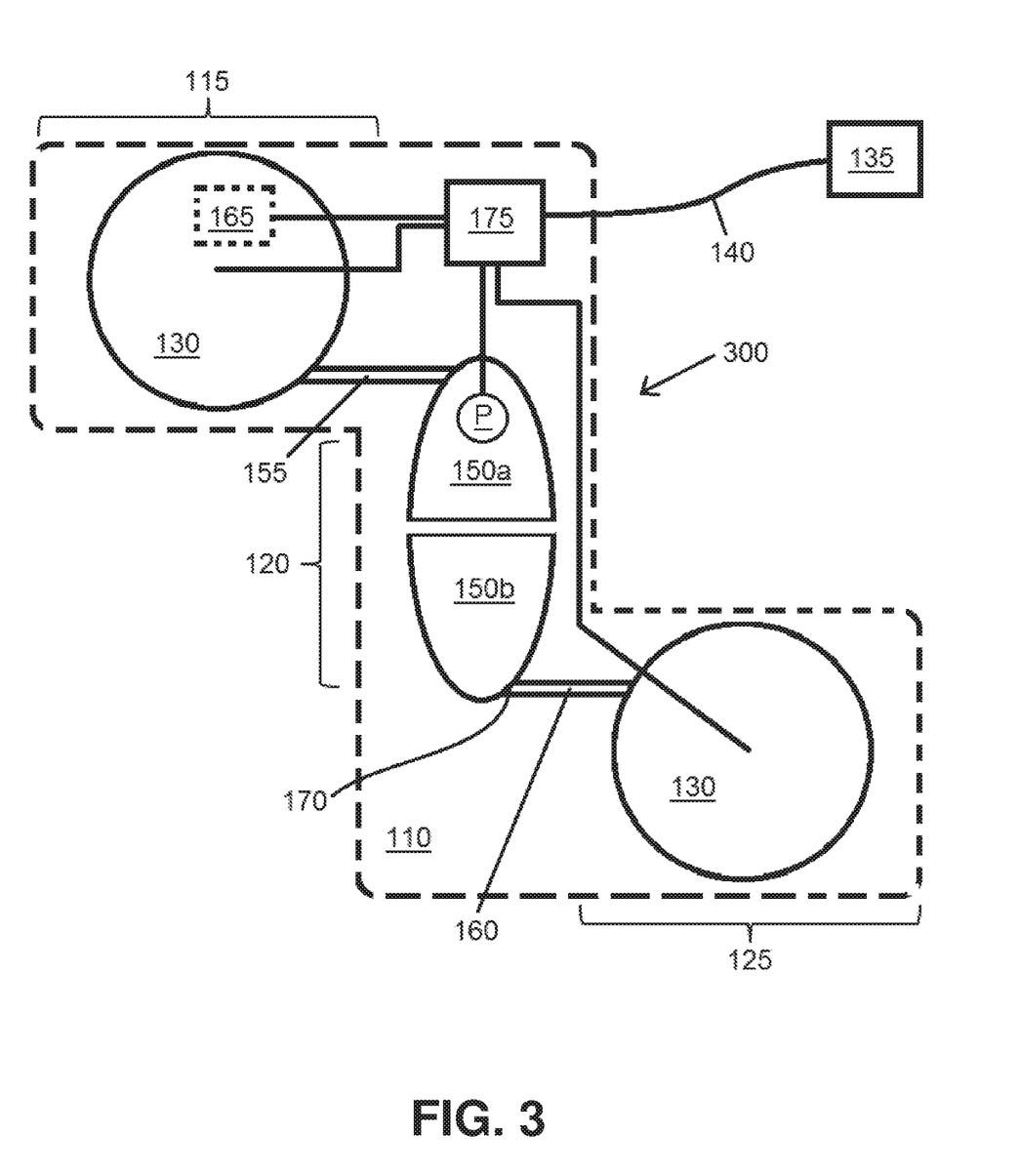
FIG. 3 is a schematic illustration of another electrode system.

In an alternative embodiment, indicated generally at 300 in FIG. 3, the electrode system includes a pair of gel reservoirs 150a, 150b, each configured to supply conductive gel to a single electrode 130. Other embodiments may include more than two gel reservoirs and/or more than two electrodes.

In some embodiments, the electrode system includes one or more sensors which provide an indication of release of the conductive electrode gel from the gel reservoir(s). For example, as illustrated in FIG. 3, the compression device 120 may include a pressure sensor P disposed within a gel reservoir. The pressure sensor may provide a signal to the controller indicative of a pressure applied to the compression device. The controller may compare a pressure calculated from the signal from the pressure sensor against a threshold pressure which is expected to cause release of conductive electrode gel from the gel reservoir. If the pressure calculated from the signal from the pressure sensor did not exceed the threshold, the controller would, for example, provide an indication of a fault, instruct a CPR administrator to apply greater pressure to the compression device, or send a signal to open a valve to allow the conductive electrode gel to flow from the gel reservoir(s) to the electrode(s). In another embodiment, the conductive electrode gel is retained within the gel reservoir under pressure. Release of the conductive electrode gel from the gel reservoir results in a reduced pressure within the gel reservoir. A signal supplied from the pressure sensor to the controller indicative of a pressure below a threshold pressure would indicate to the controller that the conductive electrode gel had been released from the gel reservoir.

In other embodiments, one or both therapy pads may include a conductivity sensor 165 disposed, for example, on a bottom surface of the electrode. The conductivity sensor 165 would indicate a lower conductivity in the presence of the conductive electrode gel than in the absence of the conductive electrode gel. The conductivity sensor 165 provides a conductivity signal to the controller 135 indicative of the presence or absence of the conductive electrode gel at the electrode. If the conductivity signal was indicative of the absence of the conductive electrode gel at the electrode, the controller would, for example, provide an indication of a fault, instruct a CPR administrator to apply greater pressure to the compression device, or send a signal to open a valve to allow the conductive electrode gel to flow from the gel reservoir(s) to the electrode(s). Alternatively still, in other embodiments, the controller may make an impedance measurement of the impedance between the electrodes (and including the subject) both before and after attempted deployment of the electrode gel to verify the presence and deployment of the electrode gel.

In another embodiment, a membrane or valve 170 disposed, for example, in one or both of the conduits 155, 160 may provide a signal to the controller indicative of whether the membrane or valve 170 had been ruptured or opened to provide for the passage of the conductive gel. For example, the membrane or valve 170 may include a thin conductor which is severed upon opening of the membrane or valve 170, providing a change in resistance which may be detected by the controller 135. If the signal from the membrane or valve 170 was indicative of the conductive electrode gel not having been released, the controller would, for example, provide an indication of a fault, instruct a CPR administrator to apply greater pressure to the compression device, or send a signal to open a valve to allow the conductive electrode gel to flow from the gel reservoir(s) to the electrode(s).

In further embodiments, responsive to the detection of the application of CPR to a subject, for example, by signals provided from the accelerometer to the controller, the controller may cause the conductive electrode gel to flow to the electrodes 130 by the application of a pressurized gas to the inside of the gel reservoir(s), for example, as described in U.S. Pat. No. 5,078,134, titled PORTABLE DEVICE FOR SENSING CARDIAC FUNCTION AND AUTOMATICALLY DELIVERING ELECTRICAL THERAPY, issued Jan. 7, 1992, which is incorporated by reference herein in its entirety.

The controller 135 generally includes at least one processor, microprocessor, or controller, such as a processor commercially available from companies such as Texas Instruments, Intel, AMD, Sun, IBM, Motorola, Freescale and ARM Holdings. In some embodiments, the at least one processor of the controller 135 is configured to monitor the patient's medical condition, to perform medical data logging and storage, and/or to provide medical treatment to the patient in response to a detected medical condition, such as cardiac arrhythmia. Although not shown, the electrode system may include additional sensors capable of monitoring the physiological condition or activity of the patient. For example, sensors capable of measuring blood pressure, heart rate, thoracic impedance, pulse oxygen level, respiration rate, heart sounds, and the activity level of the patient may also be provided.

It is to be understood that the electrode systems and electrodes described herein are not limited to the shapes, sizes, or configurations illustrated. For example, although illustrated as disks, the electrodes 130 may alternatively be in the shape of rectangles or other shapes. Electrode systems may include more than a single electrode in a therapy pad and may include more than one therapy pad. Gel reservoirs as described herein may supply conductive electrode gel to more than one electrode and electrodes may be supplied conductive electrode gel from more than one gel reservoir.

Figure 4:
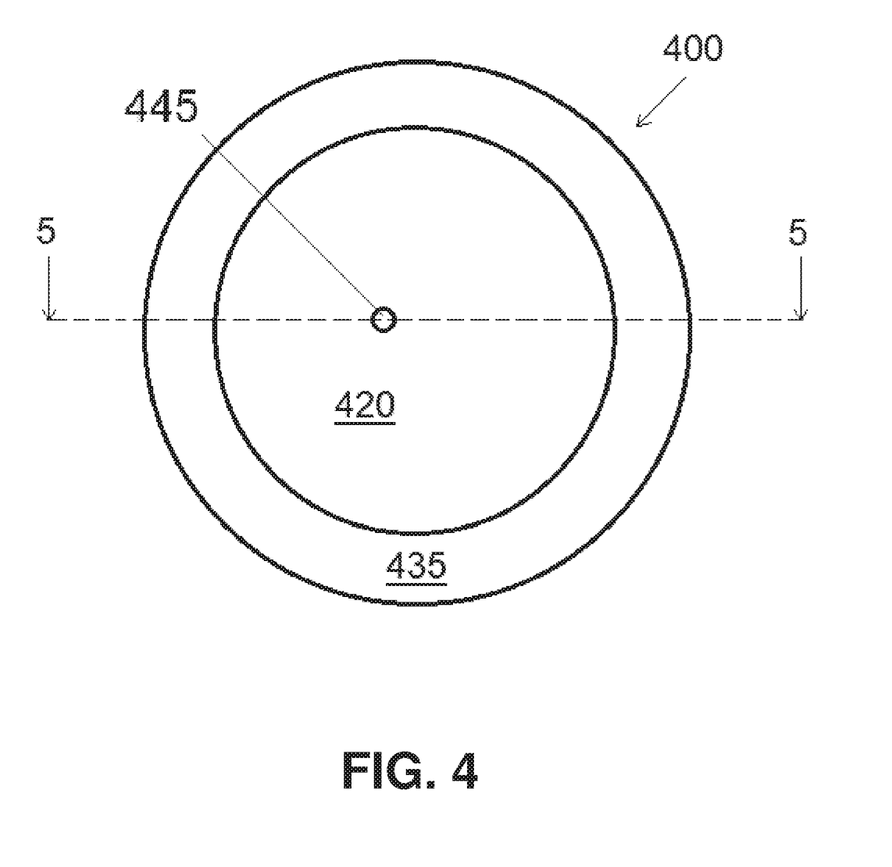
FIG. 4 is a plan view of an electrode.
Figure 5:
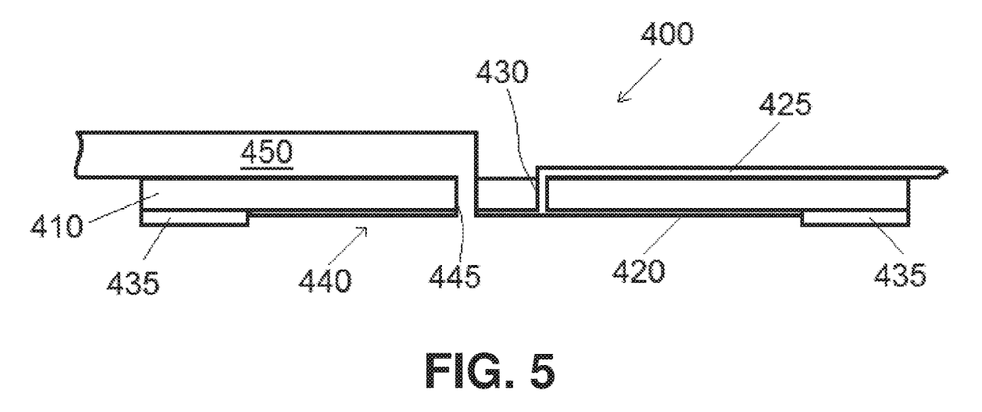
FIG. 5 is a cross sectional view of the electrode of FIG. 4.

An embodiment of an electrode 400 which may be used with electrode systems as described herein or with other electrode systems is illustrated in plan view from a front side (i.e., the side of the electrode to be adjacent the skin of the subject) in FIG. 4 and in cross section through line 5-5 of FIG. 4 in FIG. 5. The electrode includes a backing layer 410 (FIG. 5) which may be formed of a flexible, waterproof, yet breathable material that permits the passage of water vapor away from the subject. Suitable materials may include, for example, polyurethane or Tegaderm™ wound care dressings (3M, St. Paul, Minn., USA), expanded polytetrafluoroethylene, for example, Gore-Tex® (W. L. Gore & Associates, Inc., Elkton, Md., USA), or other non-woven polymers. The backing layer 410 includes a front surface configured to adhere to the skin of a subject and a rear surface. A plate 420 includes a rear surface coupled to the front surface of the backing layer and a front surface that includes a conductive material layer. The conductive material layer may include, for example, a silver/silver chloride alloy. The plate 420 is, in some embodiments, formed from a conductive material, for example, a metal or conductive polymer. An electrical lead 425 is provided in electrical contact with the conductive material layer of the plate, for example, by passing through an aperture 430 through the backing layer 410. The electrical lead extends to a controller configured to deliver charge to the electrode and/or monitor a signal from the electrode. The electrical lead 425 is illustrated as extending across the rear of the electrode backing layer, but in other embodiments may extend across the front or may be embedded in the electrode backing layer.

The electrode 400 further includes an adhesive film layer 435 coupled to the front side of the electrode. The adhesive film layer forms a closed geometric shape, for example, a ring. The adhesive film layer, in combination with the plate 420, defines a conductive gel cavity 440. The conductive gel cavity 440 is surrounded on all sides by the adhesive film layer in a plane substantially parallel to the front surface of the backing layer. A gel conduit 450, which in some embodiments may be similar to one of conduits 155, 160, is fluidly connected to a source of conductive electrode gel, for example gel reservoir 150 of FIG. 1. The gel conduit 450 is also in fluid communication with the conductive gel cavity 440 through an aperture 445 in the electrode. In use, a conductive electrode gel would flow through the gel conduit 450 and into the conductive gel cavity 440 through the aperture 445 to provide a low resistance electrical path between the conductive material layer of the plate 420 and the skin of a subject to which the electrode 400 is attached to facilitate, for example, providing defibrillation to the subject with the electrode.

Figure 6:
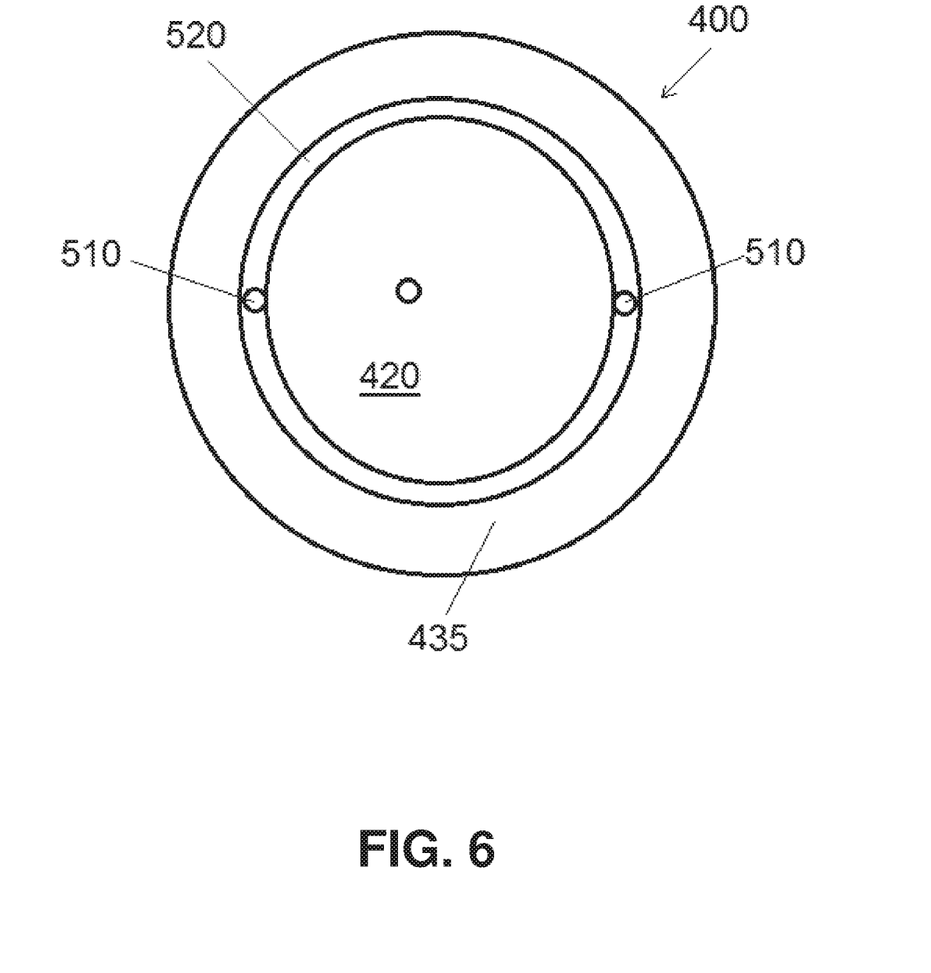
FIG. 6 is a plan view of another electrode.
Figure 7:
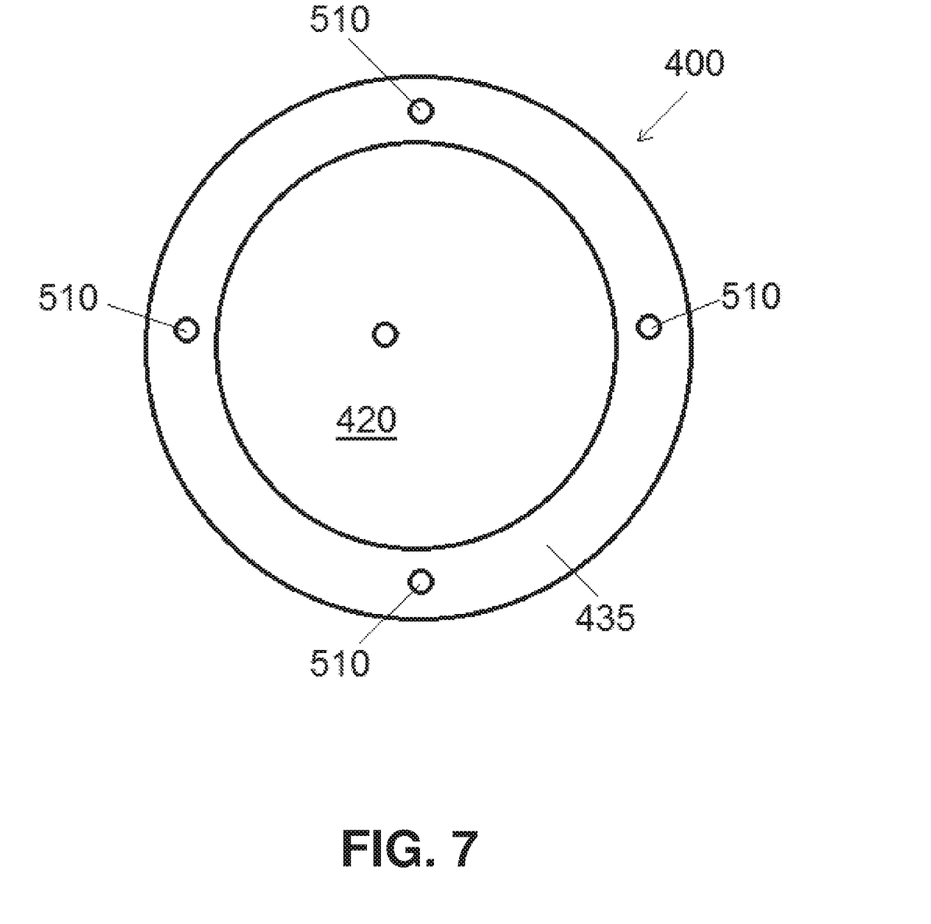
FIG. 7 is a plan view of another electrode.

The adhesive film layer 435 facilitates retaining the electrode in contact with the skin of a subject and also confines conductive electrode gel within the conductive gel cavity 440. The adhesive film layer may include any form of adhesive that is capable of securing the electrode to the skin of a subject. For example, the adhesive film layer 435 includes, in some embodiments, a light curable adhesive. In some embodiments, the adhesive film layer 435 includes an ultraviolet (UV) light curable adhesive. In some embodiments, the electrode may be placed on the skin of a subject and exposed to ultraviolet light or light of a different frequency to cure the adhesive. In some embodiments, a source of light for curing the adhesive, for example a source of ultraviolet light, is included in an electrode system housing the electrode, or in the electrode itself. As illustrated in FIG. 6, the electrode may include one or more light emitting diodes (LEDs) 510, for example, UV LEDs positioned proximate the light curable adhesive of the adhesive film layer 435. The one or more LEDs 510 are, in some embodiments, optically coupled to a light pipe or guide 520. The light pipe or guide 520 directs light from the LED(s) to portions of the adhesive film layer 435 which might not otherwise be exposed to sufficient light from the LED(s) to cure. The light pipe or guide 520 facilitates the curing of the light curable adhesive of the adhesive film layer 435 with the light provided by the one or more LEDs 510. In some embodiments, as illustrated in FIG. 7, the LEDs 510 and/or light pipe or guide 520 (not illustrated in FIG. 7) are embedded in the adhesive film layer 435 rather than positioned proximate an edge of the adhesive film layer 435 as in FIG. 6.

In use, the one or more LEDs 510 are activated to cure the light curable adhesive after the electrode has been positioned in place on the skin of a subject. The one or more LEDs 510 are in one embodiment activated by the controller 135, and in other embodiments activated by a separate switch and/or independent power supply. In some embodiments the electrode 400 includes a pressure sensor or switch which activates the one or more LEDs 510 upon application of more than a threshold pressure to the electrode against the skin of a subject.

The adhesive film layer 145 may alternatively or additionally include one or more forms of adhesive other than a light curable adhesive. For example, the adhesive film layer 145 includes, in some embodiments, epoxy.

Figure 8A:
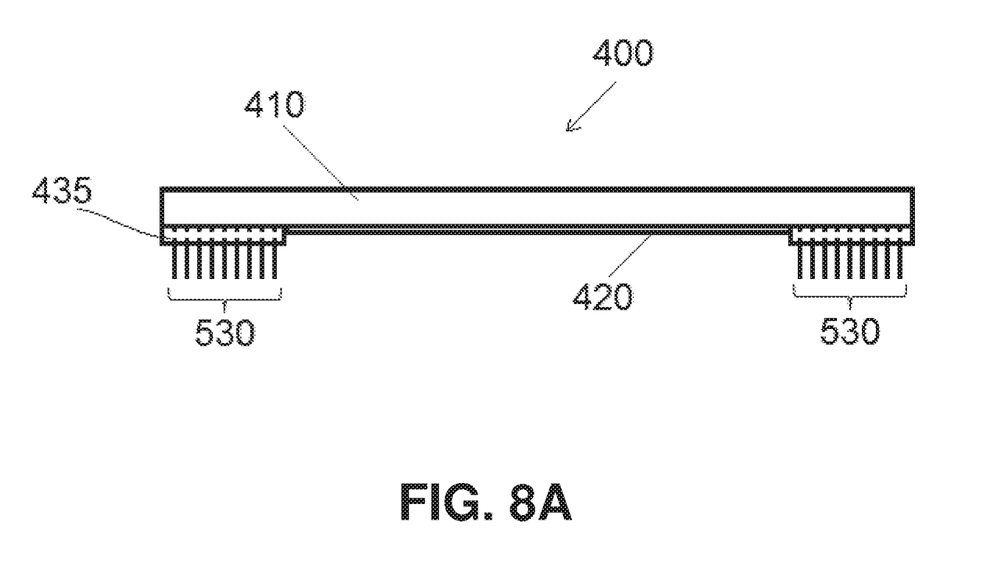
FIG. 8A is a cross sectional view of another electrode.
Figure 8B:
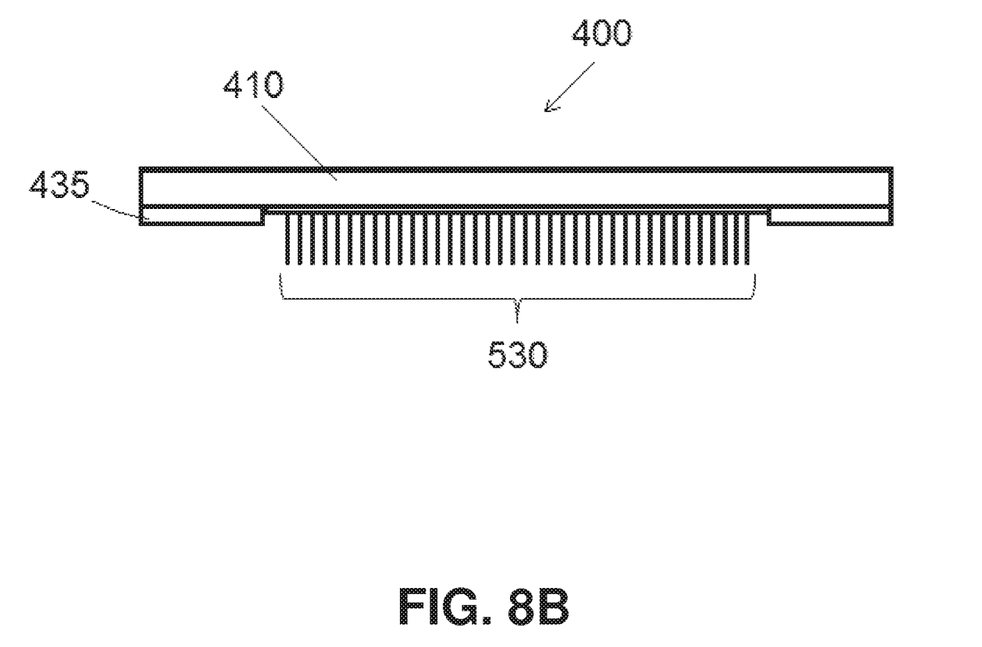
FIG. 8B is a cross sectional view of another electrode.

Embodiments of the electrode may include one or more additional features which facilitate retaining the electrode in place on the skin of a subject. For example, as illustrated in FIG. 8A, where features such as the electrical lead 425 and gel conduit 450 have been omitted for clarity, the electrode 400 may include a plurality of protrusions 530. The protrusions 530 may extend through the adhesive film layer 435. Additionally or alternatively, the protrusions may be present on another portion of the electrode, for example, on a portion of the backing 410 extending beyond the external border of the adhesive material layer and/or in an inner region of the electrode as illustrated in FIG. 8B. The protrusions 530 may additionally or alternatively be present on a surface of a therapy pad including the electrode and positioned proximate the electrode to facilitate retaining the electrode in place on the skin of the subject.

The protrusions 530 are, in some embodiments, barbs configured to penetrate an outer surface of the skin of a subject. In some embodiments the barbs are formed of a biodegradable material which breaks down when inserted into the skin of a subject after a period of, for example, about one day. In some embodiments, the barbs comprise a conductive material, for example, metal wires or carbon nanotubes or nanofibers, and in some embodiments are configured to conduct an electrical charge into the subject during, for example, defibrillation of the subject.

Figure 9:
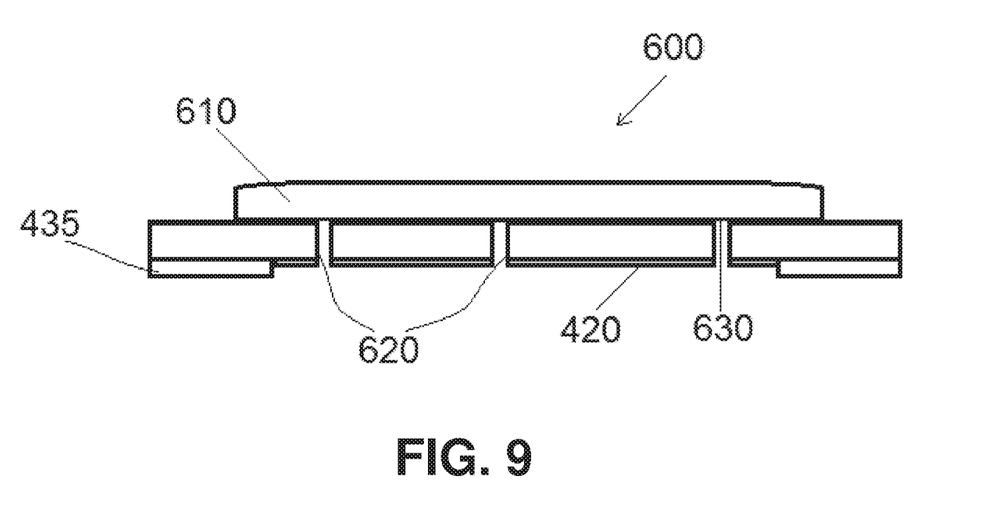
FIG. 9 is a cross sectional view of another electrode.

In a further embodiment, illustrated generally at 600 in FIG. 9, an electrode may include an integral electrode gel reservoir 610 rather than being in fluid communication with a separate gel reservoir. The integral electrode gel reservoir 610 may be formed on the rear surface of the backing layer and may deliver conductive electrode gel into the conductive gel cavity 440 through an aperture or apertures 620. The aperture or apertures 620 in some embodiments are covered by a thin membrane 630, for example, a polymer film that ruptures upon application of pressure to the electrode gel reservoir to allow the passage of conductive electrode gel.

Figure 10:
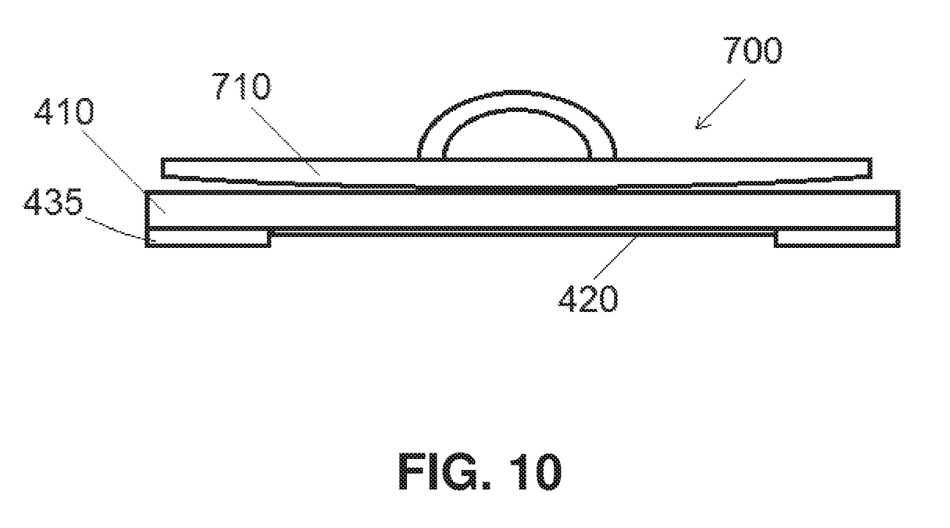
FIG. 10 is a cross sectional view of another electrode and an applicator for the electrode.

In a further embodiment, illustrated generally at 700 in FIG. 10, the electrode system may include an applicator 710 for aiding attachment of the electrode(s) to the skin of a subject. The applicator 710 may be removably coupled to the electrode with magnets, hook and loop fasteners, snaps, tabs and slots, or any other form of connector known in the art. Alternatively, the applicator may simply be provided as part of the electrode system and used to adhere each electrode to the body of the subject. The applicator 710 includes a convex surface on a side of the applicator configured to contact the rear surface of the electrode. When a user applies the electrode to the skin of a subject using the applicator, the applicator first directs pressure to a central region of the electrode. Application of additional pressure to the applicator causes the direction of force applied to the electrode to move radially outward from the center of the electrode. The application of force first to the center of the electrode and then to portions of the electrode radially offset from the center also facilitates the removal of air from between the electrode and the skin of a subject to which the electrode is applied and helps ensure the electrode conforms to the skin of the subject as closely as possible. The applicator may be removed from the electrode once the electrode is attached to the skin of a subject and the conductive electrode gel suitably distributed.

Having thus described several aspects of at least one embodiment of this invention, it is to be appreciated various alterations, modifications, and improvements will readily occur to those skilled in the art. For example, it is to be appreciated that any of the features of any of the embodiments disclosed herein may be combined or substituted for features of any other embodiment disclosed herein. Such alterations, modifications, and improvements are intended to be part of this disclosure, and are intended to be within the scope of the invention. Accordingly, the foregoing description and drawings are by way of example only.

What is claimed is:

1. An electrode system comprising:
a first therapy pad having a front surface configured to be placed in contact with skin of a patient and a back surface, the first therapy pad configured to deliver a defibrillation pulse;
a first gel reservoir fluidly connected to the first therapy pad and configured to retain a conductive gel and to release the conductive gel responsive to compressive force applied to the first gel reservoir; and
a plurality of protrusions extending from the front surface of the first therapy pad and configured to conduct an electrical charge into the patient during delivery of the defibrillation pulse,
wherein delivery of chest compressions to the patient by a CPR administrator causes the first gel reservoir to release the conductive gel therefrom to the front surface of the first therapy pad, and
wherein the first therapy pad includes:
a backing layer having a front surface configured to adhere to skin of the patient and a rear surface forming the back surface of the first therapy pad;
a plate having a rear surface coupled to the front surface of the backing layer and a front surface that includes a conductive material layer;
an electrical lead in electrical contact with the conductive material layer; and
an adhesive film border formed on the front surface of the backing layer and defining a conductive gel cavity, the conductive gel cavity surrounded by the adhesive film border on all sides in a plane substantially parallel to the front surface of the backing layer, the conductive gel cavity in fluid communication with the first gel reservoir.

2. The system of claim 1, wherein the plurality of protrusions are configured to retain the first therapy pad in place on the skin of the patient.

3. The system of claim 1, where the plurality of protrusions comprise barbs configured to penetrate an outer surface of the skin of the patient.

4. The system of claim 3, wherein the barbs are biodegradable.

5. The system of claim 3, wherein the barbs are conductive.

6. The system of claim 1, wherein the plurality of protrusions comprise carbon nanofibers.

7. The system of claim 1, wherein the plurality of protrusions extend through the adhesive film border.

8. The system of claim 1, wherein the plurality of protrusions are provided on a portion of the front surface of the backing layer beyond the adhesive film border.

9. The system of claim 1, wherein the plurality of protrusions are provided on the front surface of the plate.

10. The system of claim 1, further comprising: a chest compression sensor associated with the first gel reservoir and separate from the first therapy pad, the chest compression sensor configured to be placed on a chest of the patient and to be compressed during delivery of chest compressions to the patient by the CPR administrator.

11. The system of claim 10, wherein the delivery of the chest compressions to the patient by the CPR administrator at the chest compression sensor compresses the first gel reservoir.

12. The system of claim 10, wherein the chest compression sensor comprises an accelerometer configured to sense information representative of the chest compressions applied to the patient.

13. The system of claim 1, further comprising a sensor configured to provide an indication of release of the conductive gel from the first gel reservoir.

14. The system of claim 13, wherein the sensor comprises a conductivity sensor disposed within the first therapy pad.

15. The system of claim 13, wherein the sensor comprises a pressure sensor disposed in the first gel reservoir.

16. The system of claim 13, wherein the sensor comprises a valve disposed between the first gel reservoir and the first therapy pad.

17. The system of claim 1, further comprising a first conduit extending from the first gel reservoir and being configured for fluidly connecting the first gel reservoir to the first therapy pad.

18. The system of claim 17, wherein the first conduit extends from the first gel reservoir in a first direction which is substantially orthogonal to a direction of the compressive force applied to the first gel reservoir.

19. The system of claim 18, further comprising a second therapy pad.

20. An electrode system comprising:
a first therapy pad having a front surface configured to be placed in contact with skin of a patient and a back surface, the first therapy pad configured to deliver a defibrillation pulse;
a first gel reservoir fluidly connected to the first therapy pad and configured to retain a conductive gel and to release the conductive gel responsive to compressive force applied to the first gel reservoir;
a plurality of protrusions extending from the front surface of the first therapy pad and configured to conduct an electrical charge into the patient during delivery of the defibrillation pulse;
a first conduit extending from the first gel reservoir and being configured for fluidly connecting the first gel reservoir to the first therapy pad, the first conduit extending from the first gel reservoir in a first direction which is substantially orthogonal to a direction of the compressive force applied to the first gel reservoir;
a second therapy pad; and
a second conduit fluidly connecting the first gel reservoir to the second therapy pad, the second conduit extending from the first gel reservoir in a second direction which is substantially orthogonal to the direction of the compression of the first gel reservoir, the first direction being different from the second direction,
wherein delivery of chest compressions to the patient by a CPR administrator causes the first gel reservoir to release the conductive gel therefrom to the front surface of the first therapy pad.

21. The system of claim 20, wherein the conductive gel is a first conductive gel and wherein the system further includes a second gel reservoir in fluid communication with the second therapy pad, the second gel reservoir configured to retain a second conductive gel and to release the second conductive gel responsive to compression of the second gel reservoir.

22. The system of claim 20, wherein the plurality of protrusions are configured to retain the first therapy pad in place on the skin of the patient.

23. The system of claim 20, wherein the plurality of protrusions comprise barbs configured to penetrate an outer surface of the skin of the patient.

24. The system of claim 23, wherein the barbs are biodegradable.

25. The system of claim 23, wherein the barbs are conductive.

26. The system of claim 20, wherein the plurality of protrusions comprise carbon nanofibers.

27. The system of claim 20, further comprising: a chest compression sensor associated with the first gel reservoir and separate from the first therapy pad, the chest compression sensor configured to be placed on a chest of the patient and to be compressed during delivery of chest compressions to the patient by the CPR administrator.

28. The system of claim 27, wherein the delivery of the chest compressions to the patient by the CPR administrator at the chest compression sensor compresses the first gel reservoir.

29. The system of claim 27, wherein the chest compression sensor comprises an accelerometer configured to sense information representative of the chest compressions applied to the patient.

30. The system of claim 20, further comprising a sensor configured to provide an indication of release of the conductive gel from the first gel reservoir.

31. The system of claim 30, wherein the sensor comprises a conductivity sensor disposed within the first therapy pad.

32. The system of claim 30, wherein the sensor comprises a pressure sensor disposed in the first gel reservoir.

* * * * *